(12) United States Patent
Vasconcellos

(10) Patent No.: US 9,480,596 B2
(45) Date of Patent: Nov. 1, 2016

(54) THERMAL BREAST PAD DEVICE

(71) Applicant: Nicole Marie Vasconcellos, Homestead, FL (US)

(72) Inventor: Nicole Marie Vasconcellos, Homestead, FL (US)

( * ) Notice: Subject to any disclaimer, the term of this patent is extended or adjusted under 35 U.S.C. 154(b) by 14 days.

(21) Appl. No.: 14/149,320

(22) Filed: Jan. 7, 2014

(65) Prior Publication Data
US 2015/0359665 A1 Dec. 17, 2015

(51) Int. Cl.
*A61F 7/00* (2006.01)
*A61F 7/02* (2006.01)

(52) U.S. Cl.
CPC .......... *A61F 7/02* (2013.01); *A61F 2007/0019* (2013.01); *A61F 2007/0021* (2013.01); *A61F 2007/0207* (2013.01); *A61F 2007/0231* (2013.01); *A61F 2007/0242* (2013.01); *A61F 2007/0268* (2013.01)

(58) Field of Classification Search
CPC ............. A61F 7/02; A61F 2007/0018; A61F 2007/0019; A61F 2007/0021; A61F 2007/0207; A61F 2007/0268
See application file for complete search history.

(56) References Cited

U.S. PATENT DOCUMENTS

| | | | | |
|---|---|---|---|---|
| 5,050,595 A * | 9/1991 | Krafft | ...................... | A61F 7/007 450/38 |
| 5,133,348 A * | 7/1992 | Mayn | ........................ | A61F 7/10 383/901 |
| 5,304,215 A * | 4/1994 | MacWhinnie | ............ | A61F 7/02 450/38 |
| 5,427,563 A * | 6/1995 | Manning | ................... | A61F 7/02 2/73 |
| 5,507,794 A * | 4/1996 | Allen | ........................ | A61F 7/02 126/204 |
| 6,063,110 A * | 5/2000 | Stedman | ................... | A61F 7/02 607/108 |
| 6,241,715 B1 * | 6/2001 | Houser | ..................... | A61F 7/02 450/37 |
| 6,394,879 B1 * | 5/2002 | Paige | .................... | A41C 3/0064 450/1 |
| 6,464,717 B1 * | 10/2002 | Smith | ....................... | A61F 7/02 450/58 |
| 7,081,034 B1 * | 7/2006 | Zoellner | .................. | A41C 3/04 2/104 |
| 7,275,977 B1 * | 10/2007 | Rhodes | ................ | A41C 3/0064 450/38 |
| 7,309,275 B1 * | 12/2007 | Morales | .................... | A41C 3/02 450/38 |
| 7,448,936 B1 * | 11/2008 | Kemp-Dorsey | ......... | A41C 3/04 450/36 |
| 8,167,924 B2 * | 5/2012 | Rosenbaum | .............. | A61F 7/00 450/86 |
| 9,144,514 B2 * | 9/2015 | Enderby | .................... | A61F 7/08 |
| 2002/0198580 A1 * | 12/2002 | Clayton | .................... | A61F 7/02 607/109 |
| 2004/0147989 A1 * | 7/2004 | Terakita | ..................... | A61F 7/02 607/108 |
| 2005/0075706 A1 * | 4/2005 | Mayrhofer | ................. | A61F 7/02 607/96 |
| 2006/0129212 A1 * | 6/2006 | Halvorson | ................ | A61F 7/02 607/96 |
| 2010/0048098 A1 * | 2/2010 | Rosario | ................ | A41C 3/0035 450/57 |
| 2010/0298914 A1 * | 11/2010 | Rosenbaum | ............. | A61F 7/00 607/108 |
| 2014/0188199 A1 * | 7/2014 | Enderby | .................... | A61F 7/08 607/108 |
| 2015/0351956 A1 * | 12/2015 | Enderby | .................... | A61F 7/08 607/108 |

* cited by examiner

*Primary Examiner* — Kaitlyn Smith
(74) *Attorney, Agent, or Firm* — Ruben Alcoba, Esq.

(57) ABSTRACT

A thermal breast pad device that comprises of two straps that connect to each other via hook and loop materials, each strap has a pear shaped thermal pad disclosed on one end of each strap, each thermal pad defines a pear shaped aperture within each thermal pad and is split at a central location of each pear shaped thermal pad. Each pear shaped thermal pad is segmented into pockets that are evenly distributed. The pockets may be filled with flax seeds. The device can be used by nursing mothers, menstruating women, or women suffering from breast cancer that need a hot or cold compress to be draped around their breasts.

8 Claims, 5 Drawing Sheets

THERMAL BREAST PAD DEVICE

CROSS REFERENCE

This application claims the benefit of the filing dates of U.S. Provisional Patent Application No. 61/848,625, filed on Jan. 8, 2013, titled Mommy Soothers, the disclosure of which is incorporated herein by reference.

FIELD OF THE INVENTION

This invention relates to a thermal breast pad device and more particularly to a reusable therapeutic breast pad device for heating and/or cooling the female breast to alleviate the symptoms of dogged milk ducts, mastitis or engorgement.

BACKGROUND

According to the January 2013 U.S. Census Report, a baby will be born every 8 seconds. That's approximately 11,000 babies a day! Immediately after the intense labor pain, a mother is expected to breast feed her newborn. First time mothers might think the pain is done once the baby is out, yet seasoned mothers can tell you the next hurdle that must be overcome is the breast-feeding of the child.

An experience that is meant to bond a mother and child can be ruined if the breast isn't taken care of properly. Decades of research have proven the fundamental that a baby's health benefits when the baby is breast fed. However, the act of breast feeding a baby can cause the mother agonizing pain and great discomfort, for a mother's milk ducts can easily become clogged, thereby causing engorgement, mastitis, and/or constant breast pain.

Doctors, nurses and lactation consultants are trained in telling patients two things known to solve the problems associated with breast-feeding; first is to apply moist warmth to the breast prior to feedings as this allows milk to flow successfully and second is to use a cold compress after feedings to help soothe the swelling and inflammation of the breast.

Unfortunately, current products on the market lack the ability to mesh together the three essential things for breast-feeding and breast pumping mothers: one is hands free comfort while promoting milk let down; two a lightweight heat cooling combo that allows the nipple to be exposed for air circulation and sensitivity issues; and three is straps around the neck to adjust and fit all women comfortably.

The thermal breast pad device of the present invention does just that, in one gel rice and corn free product, women are able to get ideal comfort, while also following doctor's orders and keeping baby well fed. Mommy's everywhere will no longer have to sit and hold two heating pads over their breast, nor they will have to sacrifice the nipple getting agitated by being covered.

The hands free device of the present invention alleviates the symptoms associated with breast feeding while simultaneously not restricting the multi-tasking breast feeding mother. Another great aspect of the present invention is the cotton filled strap around the neck; this lets the heating pad hang around the neck of the mother without causing undue discomfort.

The product is ideal for breastfeeding mothers, yet the thermal breast pad device of the present invention does have other uses. For example, during and before a women's menstrual cycle, breast tenderness is a very common pain to have, the thermal breast pad device of the present invention can alleviate the pain.

Another alternative use of the device of the present invention is to provide it to women who are suffering from breast cancer. The device can be draped over the afflicted breast areas needing a hot or cold compress.

The present invention is a thermal breast pad device that is draped over the breasts of a woman that is used to provide either a warm or a cold compress over the areas of the breast needing thermal treatment.

SUMMARY

The present invention directed toward a thermal breast pad device that is draped over the breasts of a woman to provide either a warm or a cold compress over the areas of the breast needing thermal treatment.

The present invention is a thermal breast pad device that comprises of two straps that connect to each other via hook and loop materials, each strap has a pear shaped thermal pad disclosed on one end of each strap, each thermal pad defines a pear shaped aperture within each thermal pad and is split at a central location of each pear shaped thermal pad. Each pear shaped thermal pad is segmented into pockets that are evenly distributed. In a preferred embodiment the pockets are filled with flax seeds. In a preferred embodiment, at least one strap of the present invention shall define a cotton filled pocket. The cotton filled pockets is designed to be placed in an area of each strap that is placed over the neck of the user.

The present invention is a device that functions as a two in one heat/cooling combo for the treatment of a woman's breast needing either a hot or a cold compress when nursing.

To heat the present invention, simply place both straps of the device in a microwave for 30 second intervals. When the device has been heated to the desired temperature, the device can be used by the mother to stimulate milk production and to open any clogged milk ducts. To use the device with moist warmth, before microwaving, wet a paper towel or cloth then pat down the device to moisten and then microwave for the 30 seconds.

Alternative uses for the device can be for providing a menstruating woman with a device that will alleviate any breast pain that she may be suffering due to her menstrual cycle or it can also be a device used by women suffering from breast cancer to treat swelling.

The device can also be chilled in a freezer, thereby functioning as a cold compress. When used as a cold compress, the device shall serve to relieve swelling and inflammation of the breast being treated.

The split of each thermal pad allows each thermal pad to open and close to fit the appropriate cup size of the user. This is advantageous for women whom are nursing, for women nursing tend to have one breast larger than the other.

The device is used by a user by placing the device around the neck of the user and draping each pear shaped thermal pad of the device over each breast of the user so that the nipple of each breast is not placed in contact with each thermal pad.

An object of the present invention is to provide a thermal breast pad device that can be used by a woman to either provide a warm or cold compress to the breast of the woman. Note, the device can be used to simultaneously provide one warm and one cold compress to the breasts of the woman. The device may be used by women that breast feed their babies.

Another object of the present invention is to provide a menstruating woman with a thermal device that may alleviate some of the breast pain that she may suffer due to her menstrual cycle.

A further object of the present invention is to provide a woman that may have undergone a breast procedure with a device that can either provide a warm or a cold compress to the areas that underwent or are undergoing the procedure.

DRAWINGS

These and other features, aspects, and advantages of the present invention will become better understood with regard to the previous description and drawings where:

DESCRIPTION

Figure 1:
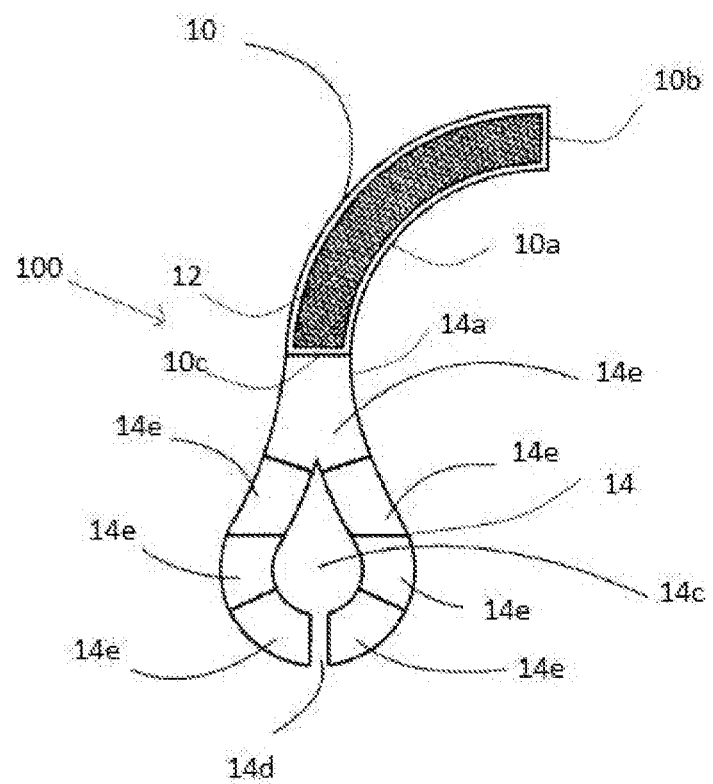
FIG. 1 is a front view of one of the straps of the present invention.
Figure 2:
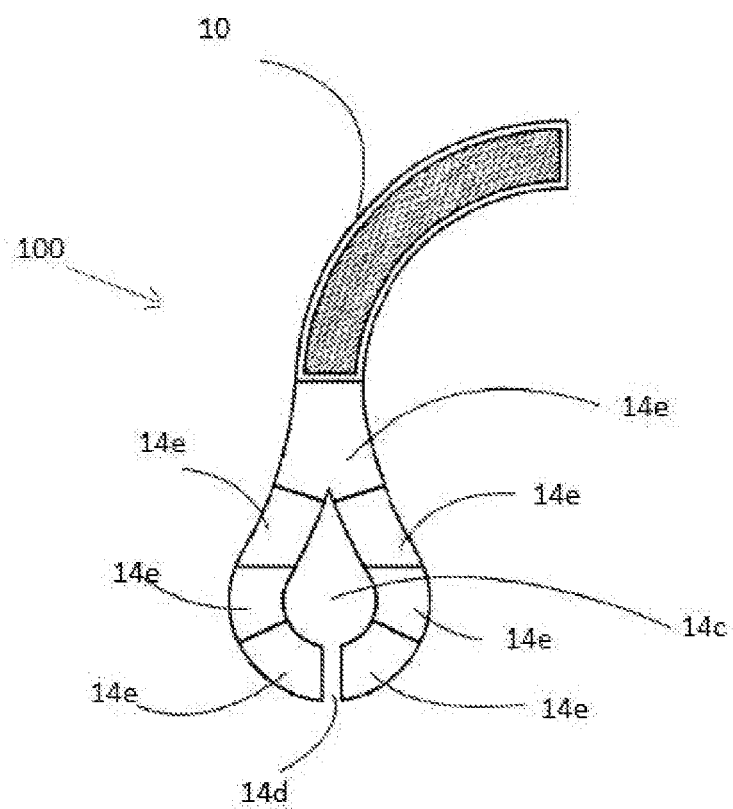
FIG. 2 is a front view of the other strap of the present invention.
Figure 3:
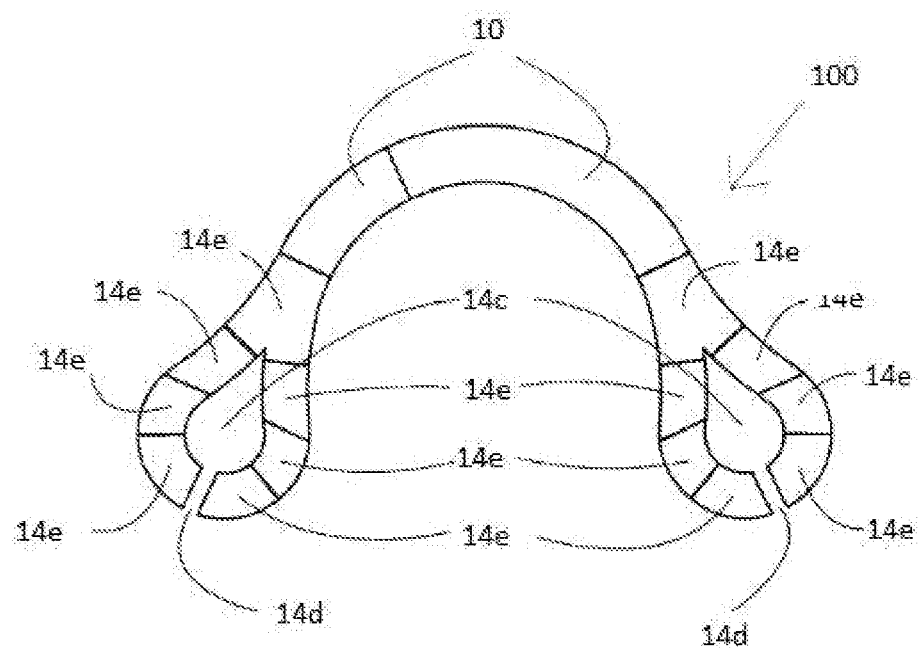
FIG. 3 is a front view of the present invention showing the thermal breast pad device of the present invention, wherein one strap of the device is attached to the other.
Figure 4:
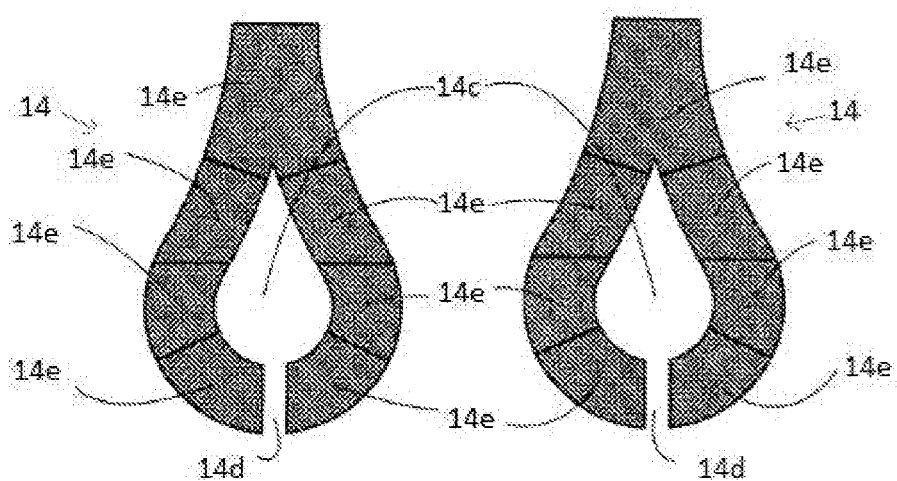
FIG. 4 is a front view of the piriform shaped thermal pads of the present invention.
Figure 5:
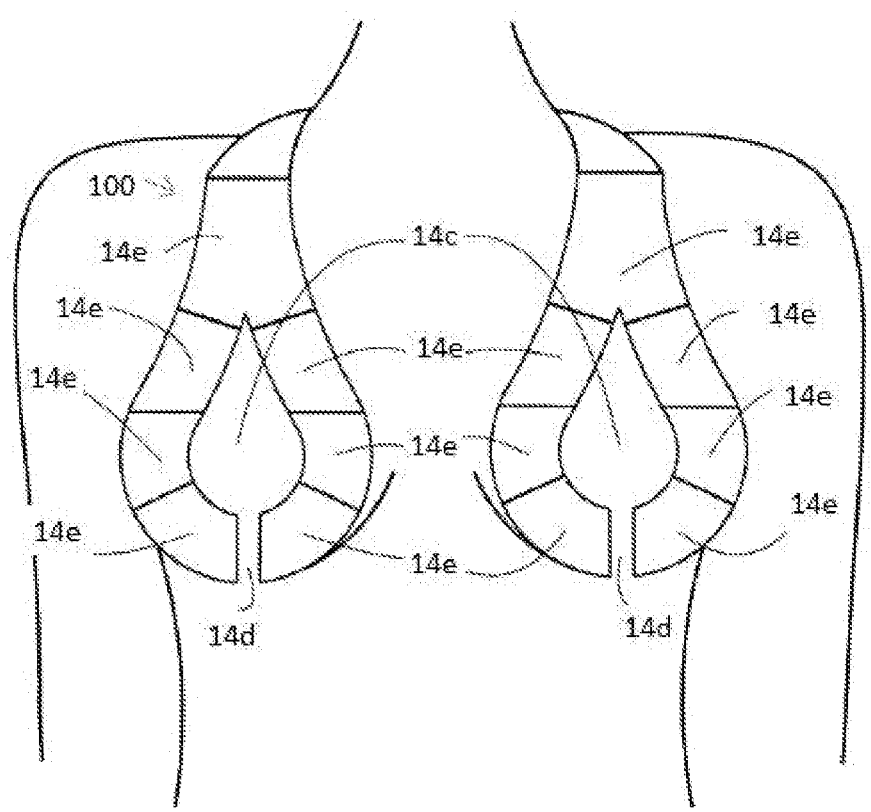
FIG. 5 is a front view showing the device on a user, and wherein the piriform shaped thermal pads of the device are draped on the breast of the user.

As seen in FIGS. 1 and 5, a thermal breast pad device 100, the breast pad device 100 having a pair of curved straps 10 having an inner curvature of at least seven inches, each curved strap 10 having a hook and loop attachment 12 running adjacent to the inner curvature 10a, the hook and loop attachment 12 of each strap 10 would be attached to the other strap 10 when the thermal breast pad device 100 is placed around a user's neck, each curved strap 10 having a first 10b and a second end 10c. The thermal breast pad device 100 further has a pair of piriform shaped thermal pads 14 having a top 14a and a bottom 14b, the top of each piriform shaped thermal pad 14a is fixedly attached to the second end of each curved strap 10c, each thermal pad 14 defines a piriform aperture 14c, the bottom of each thermal pad defines a centrally located split 14d, each thermal pad defines a plurality of pockets 14e that are spaced along each thermal pad 14, and each pocket 14e houses a thermal element (not shown in figures).

In an embodiment of the present invention, at least one of the curved straps of the thermal breast pad device 100 defines a cotton filled pocket (not shown in figures). The cotton filled pocket lies around the neck of the user when the device is worn by the user.

In a preferred embodiment of the present invention, the thermal breast pad device's 100 thermal element is flax seed.

In another embodiment of the present invention, each thermal pad 14 of the thermal breast pad device 100 has at least seven pockets 14e. The device has seven pockets 14e so that the thermal element of each pocket 14e remains in each pocket 14e of the device 100 when the device 100 is placed on a user, thereby ensuring that each pocket 14e cools or warms the breast of the user uniformly.

In another embodiment of the present invention, each pocket 14e of the thermal breast pad device 100 is at least two inches in length.

In preferred embodiments of the present invention, the device is made of a cotton material and the pockets are filled with flax seeds.

The device of the present invention is used by first providing the thermal breast pad device 100. Then, heating or cooling the thermal breast pad device 100. And lastly, placing the thermal breast pad device's thermal pad around a user's neck so that each thermal pad 14 of the thermal breast pad device 100 drapes around each breast of the user in a manner in which the nipple of the user does not make contact with each thermal pad 14 and the nipple remains exposed.

An advantage of the present invention is that it provides a thermal breast pad device that is used by a woman to either provide a warm or cold compress to the breast of the woman. Note, the device can be used to simultaneously provide one warm and one cold compress to the breasts of the woman. The device is ideal for women that are breast feeding.

Another advantage of the present invention is that it provides a menstruating woman with a thermal device that alleviates some of the breast pain that she suffers due to her menstrual cycle.

A further advantage of the present invention is that it provides a woman that has undergone a breast procedure with a device that either provides a warm or a cold compress to the areas that underwent the procedure.

Although the present invention has been described in considerable detail in reference to preferred versions, other versions are possible. Therefore, the spirit and scope of the appended claims should not be limited to the description of the preferred versions contained herein.

What is claimed is:

1. A thermal breast pad device, the thermal breast pad device comprising:
a pair of curved straps having an inner curvature of at least seven inches, each curved strap having a hook and loop attachment running adjacent to the inner curvature, wherein the hook and loop fastener attaches to the other strap when the thermal breast pad device is placed around a user's neck, each curved strap having a first and a second end; and
a pair of piriform shaped thermal pads having a top and a bottom, the top of each piriform shaped thermal pad is fixedly attached to the second end of each curved strap, each thermal pad defines a piriform aperture, the bottom of each thermal pad defines a centrally located split, each pad defines a plurality of pockets that are spaced along each thermal pad, and each pocket houses a thermal element.

2. The thermal breast pad device of claim 1, wherein at least one of the curved straps defines a cotton filled pocket.

3. The thermal breast pad device of claim 2, wherein the thermal element is flax seed.

4. The thermal breast pad device of claim 3, wherein each thermal pad has at least seven pockets.

5. The thermal breast pad device of claim 1, wherein the thermal element is flax seed.

6. The thermal breast pad device of claim 1, wherein each thermal pad has at least seven pockets.

7. The thermal breast pad device of claim 6, wherein each pocket is at least two inches in length.

8. A method of using the thermal breast pad device of claim 1, comprising the steps of:
providing the thermal breast pad device;
heating or cooling the thermal breast pad device; and
placing the thermal breast pad device around a user's neck so that each thermal pad of the thermal breast pad device drapes around each breast of the user in a manner in which the nipple of the user does not make contact with each thermal pad and the nipple remains exposed.

* * * * *